United States Patent [19]

Hoiss

[11] 4,347,877
[45] Sep. 7, 1982

[54] APPARATUS FOR ASEPTICALLY DISCHARGING FLOWABLE SUBSTANCES

[76] Inventor: Jakob Hoiss, Waldhornstrasse 31, D-8000 München 50, Fed. Rep. of Germany

[21] Appl. No.: 142,252

[22] Filed: Apr. 21, 1980

[51] Int. Cl.³ .......................... B08B 3/00; B65B 3/04; F16K 51/00
[52] U.S. Cl. ................................ 141/91; 134/166 C; 137/238
[58] Field of Search ....................... 134/166 R, 166 C; 137/238, 241, 246; 141/89, 90, 91; 222/148; 422/26, 28

[56] References Cited

U.S. PATENT DOCUMENTS 3,871,824  3/1975  Rechsteiner et al. ................. 422/28
3,998,589  12/1956  Rechsteiner et al. ................. 422/28

Primary Examiner—Frederick R. Schmidt
Attorney, Agent, or Firm—Kontler & Grimes

[57] ABSTRACT

An arrangement for aseptically discharging flowable media, especially sterilized feed solutions for use in microbiology, includes a discharge valve which has a ball-shaped valve member having a through passage in which there is accommodated an insert that carries a coupling member to which there is connected a sterilized hose in the open position of the valve member. The valve member is rotatably accommodated in a chamber of a valve housing and the flowable medium flows through the insert and the coupling member into the hose in the open position, while the coupling member is accommodated in a compartment of the housing in the closed position of the valve member. A stream of sterilizing medium, preferably steam, is admitted into the compartment in the closed position to sterilize the coupling member. The admission of the sterilizing medium is throttled as the valve member is rotated toward its open position, but maintained until the hose is connected to the coupling part. Another stream of the sterilizing medium is supplied into the output duct which leads toward the discharge valve, communicating with the duct immediately downstream of a main shutoff valve for the flowable medium which is closed during the sterilizing operation, to sterilize the duct and the region of the inlet port of the discharge valve.

18 Claims, 4 Drawing Figures

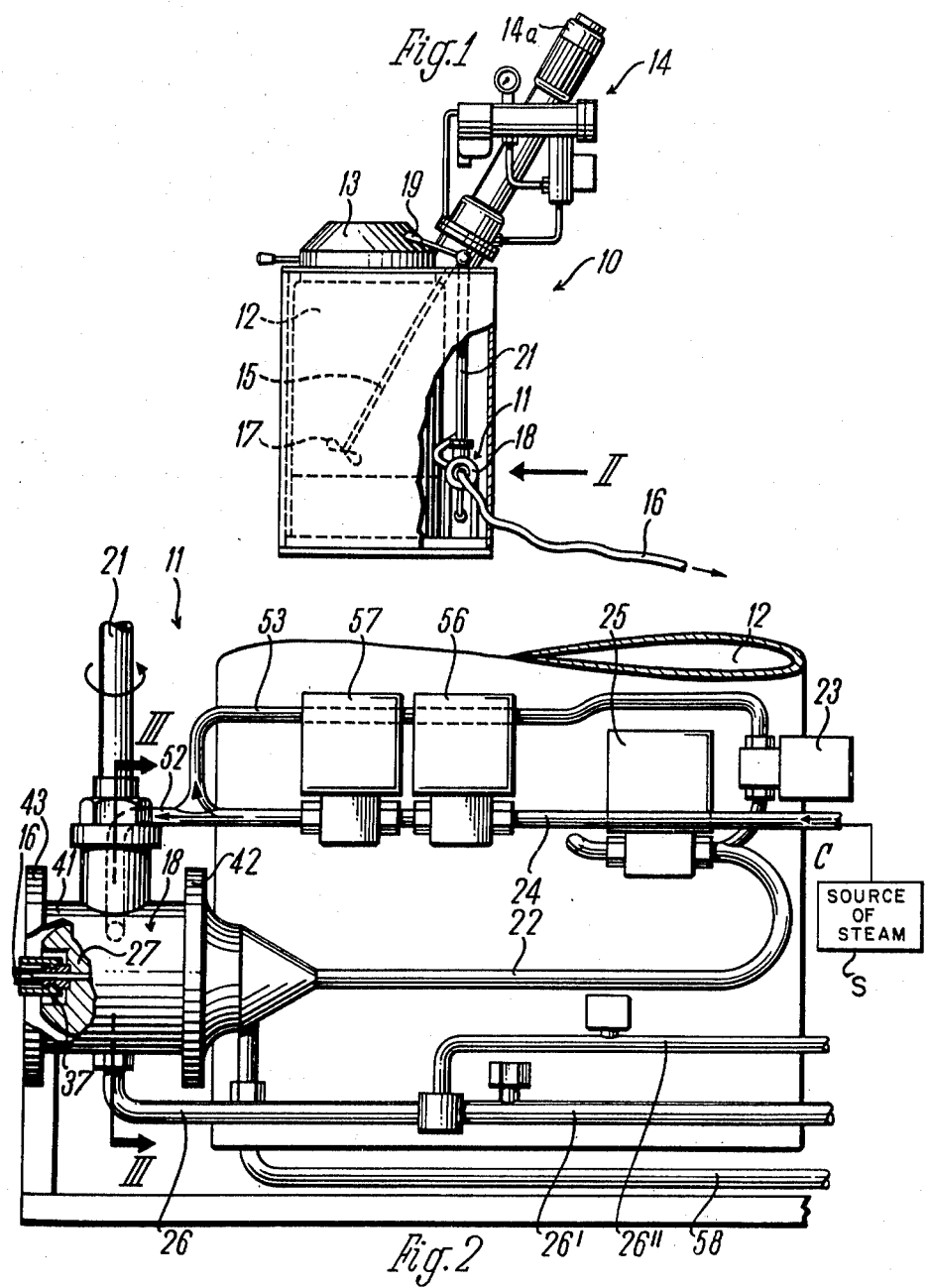

APPARATUS FOR ASEPTICALLY DISCHARGING FLOWABLE SUBSTANCES

BACKGROUND OF THE INVENTION

The present invention relates to an arrangement for aseptically discharging flowable substances, particularly such which have been sterilized in a sterilizing container, into a sterilized conduit.

In sterilizing devices, for instance such as used for the manufacture and sterilization of liquids, for example, feed solutions for use in microbiology, such as so-called agar-agar, it is of considerable significance that the filling of the sterilized liquids or substances from the device into smaller packaging units or receptacles be also achieved in a sterile or aseptic manner. The devices of this type usually operate on a discontinuous basis, such as in batches or charges, and, hence, must be cleaned following the discharge of each batch or charge, and sterilized each time anew, inclusive of the filling arrangement. Generally speaking, a hose or a similar conduit, which has also been previously sterilized, is connected to the device and serves for conducting the discharged liquid or substance from this device which is situated at a working location or in a working room, to a sterile packaging room in which the substance is admitted into the packaging receptacles.

One problem which is encountered in the conventional devices of this general type is that the connecting flange thereof which is to be connected to a cooperating connecting flange of the hose or conduit, is exposed at the working location to the ambient air at least during a time interval immediately preceding, and terminating with, the connection of the two flanges to one another. This, of course, means that a complete sterilization or maintenance of the sterile condition of the passageways in the filling arrangement is not and cannot be assured. In one heretofore known filling arrangement, the discharge valve incorporates a closing device including a poppet or disc valve which is equipped with a threaded flange rigidly provided thereon. Besides the aforementioned disadvantage that this flange cannot be maintained completely aseptic, this discharge valve is further possessed of the disadvantage that it is very difficult to cleanse or sterilize the interior thereof, inasmuch as such a poppet valve closing device includes angular and/or undercut hollow spaces into which the hot steam stream which is used for sterilization does not penetrate, among others, because of the possible turbulences or eddy currents. Consequently, the steam stream does not displace the unsterile air from these regions so that there remain such regions after the performance of this sterilizing operation which are not completely sterilized or which are not sterilized at all. This, of course, is very disadvantageous.

OBJECTS AND SUMMARY OF THE INVENTION

Accordingly, it is a general object of the present invention to avoid the disadvantages of the prior art.

More particularly, it is an object of the present invention to provide a sterilizing apparatus which is not possessed of the disadvantages of the conventional apparatus of this type.

Yet more particularly, it is an object of the present invention to devise an arrangement for aseptically discharging flowable media, which arrangement has simple contours and thus is easy to clean in the region of a connection of a filling hose or a similar conduit thereto.

A further object of the present invention is to so construct the arrangement of the type here under consideration as to be simple in construction, easy to operate, simple to sterilize, and yet reliable in operation.

In pursuance of these objects and others which will become apparent hereafter, one feature of the present invention resides in an arrangement for aseptically discharging a flowable substance, especially such which has been sterilized in a sterilizing container, into a sterilized conduit, which arrangement, briefly stated, comprises an output duct for the flowable substance having an output end; a discharge valve arranged at and communicating with the output end of the output duct and including a valve housing bounding a chamber and inlet and outlet ports for the flowable substance, and having valve seats respectively surrounding the inlet and outlet ports, and a valve member received in the chamber and having a surface located on an imaginary sphere and sealingly contacting the seats, and a through passage having inlet and outlet ends, the valve member being rotatable between an open position in which the inlet and outlet ends of the passage respectively register with the inlet and outlet ports of the valve housing, and a closed position; means for coupling the discharge valve to the sterilized conduit, including a tubular coupling member mounted on the valve member in communication with the outlet end of the passage and having a portion extending beyond the latter and terminating within the confines of the imaginary sphere; and means for admitting sterilizing medium, especially steam, between the valve housing and the valve member at the region of the coupling member. When the aseptically discharging arrangement of the present invention is constructed in this manner, it is not only as simple as possible as far as its construction is concerned, but it also renders it possible to completely sterilize even the outward region of the discharge valve to which the sterilized filling conduit is connected. A ball valve as such has the important advantage that its contour is geometrically simple, that is, that it is not provided with undercut chambers, double chambers, or the like. By modifying the shape of the ball-shaped valve member so that it directly carries the respective coupling part, it is possible to move this coupling part into an enclosed space into which a sterilized stream of the sterilizing medium, particularly steam, is admitted to fill this enclosed space.

According to an advantageous aspect of the present invention, a commercially available ball valve is being used as the discharge valve of the arrangement of the present invention, which conventional valve is converted into the discharge valve by using an insert which is mounted in the passage of the valve member and preferably rigidly connected to the valve member, the insert supporting the coupling member. This renders it possible to inexpensively manufacture the modified ball valve, that is, the ball valve which is equipped with the coupling part or into which the one coupling part is integrated. It is further proposed in accordance with the present invention to provide the insert with a frustoconical opening which converges from the inlet end of the passage toward the coupling member. When the opening of the insert is constructed in this manner, it is achieved that the sterilizing steam stream, which flows through this passage during the sterilizing operation, passes through this opening in a manner resembling flow through a jet nozzle, which again contributes to avoidance of the formation of eddy currents, turbulence or other irregularities in the flow pattern of the sterilizing medium.

The method of sterilizing an arrangement for aseptically discharging a flowable substance, especially such which has been sterilized in a sterilizing container, wherein the arrangement is of the type including an output duct for the flowable substance having a main shutoff valve at its upstream end and a ball valve having one part of a coupling to a sterilized conduit at its downstream end, comprises the steps of closing the main valve; closing the ball valve; admitting sterilizing medium at full pressure into the duct and to the region surrounding the coupling part for a predetermined period of time; reducing the pressure of the sterilizing medium upon the termination of this time period; subsequently opening the ball valve; attaching the sterilized conduit to the coupling part; discontinuing the admission of the sterilizing medium; and opening the main valve.

It will be appreciated that, when this method is resorted to, it is possible to simultaneously perform two sterilizing operations while the discharge valve assumes its closed position, that is, on the one hand, the sterilization of the discharge valve inlet and of the output duct for the flowable substance which leads from the main valve to the discharge valve and, on the other hand, the sterilization of the internal chamber of the discharge valve inclusive of the respective coupling part which is integrated into the valve member. Prior to the opening of the discharge valve, the admission of the sterilized medium, such as steam, is throttled to such an extent that the operating personnel or other people who may be present in the vicinity of the discharging valve are not injured by the escaping sterilized steam. This further throttled admission of the sterilizing steam renders it possible to keep the internal surfaces of the coupling part mounted on the valve member aseptic prior to and during the connection of the sterilized filling conduit to this coupling part. In addition thereto, also the internal chamber of the discharge valve is maintained, due to the use of such method, under the influence of the sterilizing steam, which is of a particular importance especially during the rotation of the valve member toward its open position, in view of the fact that the unsterile ambient air would otherwise be drawn into the internal chamber of the discharge valve during this rotation toward the open position. Only after the sterilized conduit is connected to the coupling part, or simultaneously with establishing this connection, is the admission of the sterilizing steam discontinued and the main shutoff valve is opened for admitting the sterilized flowable substance into the discharge valve, and through the same, into the sterilized filling conduit.

The novel features which are considered as characteristic of the invention are set forth in particular in the appended claims. The improved arrangement for aseptically discharging sterilized flowable media itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a somewhat diagrammatic and partially sectioned side elevational view of an apparatus for preparing sterilized substances, which apparatus is equipped with an aseptically discharging arrangement in accordance with the present invention;

FIG. 2 is a partially sectional side elevational view taken in the direction of the arrow II of FIG. 1 of the discharging arrangement of the present invention, drawn to a larger scale, and with a valve member in its open position.

DETAILED DESCRIPTION OF THE PREFERRED EMBODIMENT

Figure 3:
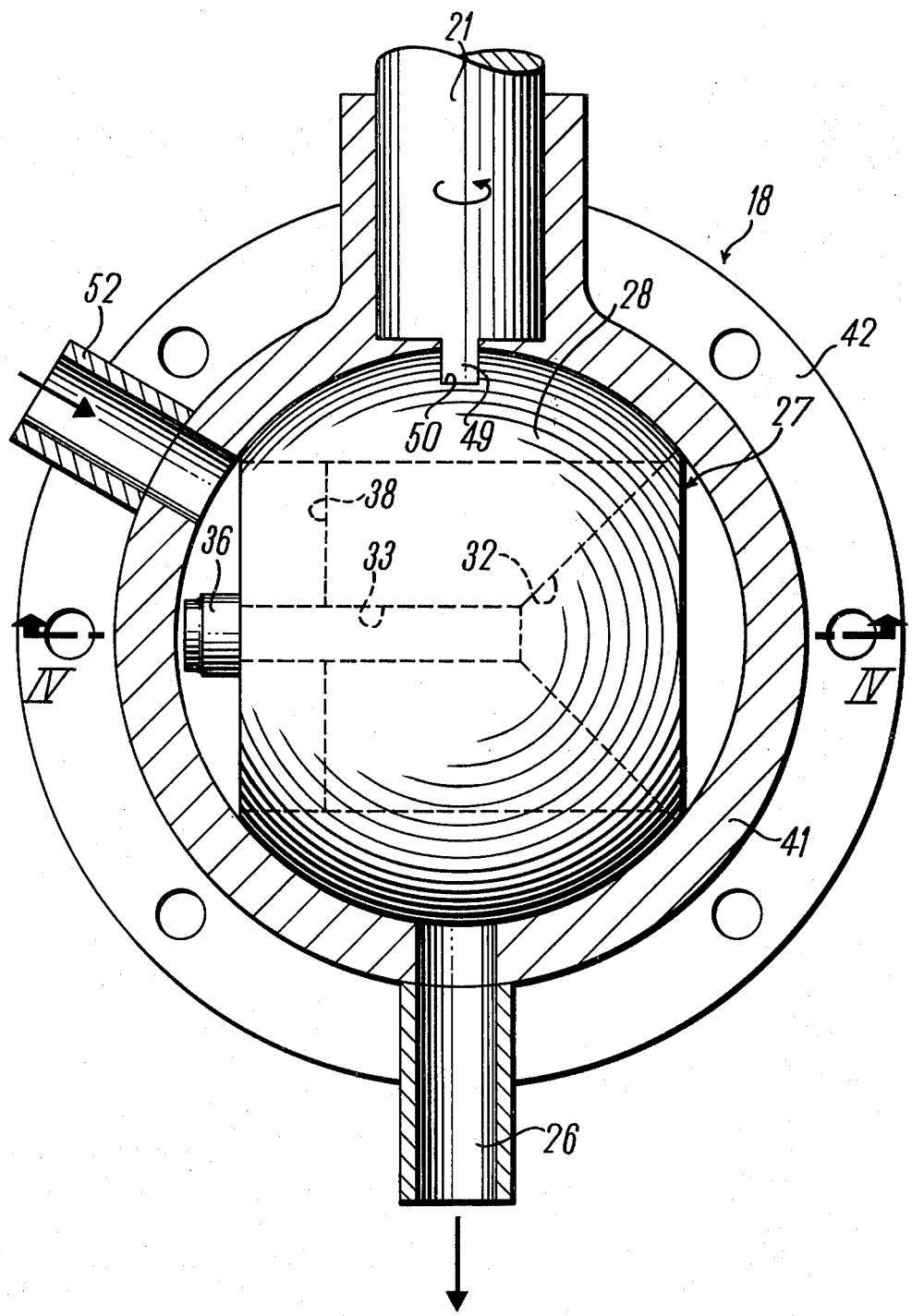
FIG. 3 is a still more enlarged cross sectional view of a part of the arrangement taken on line III—III of FIG. 2, but with the valve member assuming its closed position.

Referring now to the drawing in detail, and first to FIG. 1 thereof, it may be seen that the reference numeral 10 has been used for identifying an apparatus for producing, preparing, thermally treating and filling flowable substances, such as so-called agar-agar feeding solutions for use in microbiology. The apparatus 10 treats the respective flowable medium under sterile or aseptic conditions. As seen in FIG. 1, the apparatus 10 includes an arrangement 11 in accordance with the present invention for aseptic discharging of the thus produced flowable substance into smaller packaging units or receptacles. The appartus 10 includes a container 12 which is equipped with a closable lid 13 and with a stirring device 14 which is mounted on the lid 13 and extends into the interior of the container 12 at an acute angle to the vertical. The stirring device 14 includes a driving shaft 15 and an impeller 17, which are the only components of the stirring device 14 which extend into the interior of the container 12. FIG. 1 also illustrates a motor 14a, such an electric motor, which drives the shaft 15. The container 12 as well as the driving arrangement of the stirring device 14 are provided, in a conventional manner which has not been illustrated in the drawing, with conduits through which sterilizing not steam is admitted thereto in order to be able to sterilize these components of the apparatus 10 prior to the admission into the interior of the container 12 of the ingredients which are used for the production of flowable substance. The respective ingredients, for instance, for the feeding solution, are then introduced into the interior of the container 12 and mixed with one another while the lid 13 is in closed position in which it separates the interior from the exterior of the container 12. During this mixing operation, the container 12 is heated, by means of conventional and hence not illustrated heating elements, to a certain temperature in excess of 120° C. and the contents of the container 12 are maintained at this temperature for a predetermined time interval, as a result of which the flowable substance is sterilized. Prior to the discharging, the flowable substance which has been rendered sterile in this manner is cooled to a temperature at which it is still flowable. At the same time, the discharging arrangement 11 of the present invention is sterilized in the manner which will be discussed in more detail later on, in order to be able to effect the discharge of the flowable substance into a sterilized hose 16 under aseptic conditions.

As seen in particular in FIG. 2, the filling arrangement 11 of the present invention includes a discharge valve 18 which is positionally adjustable by means of a shaft 21 and a handle 19 located at the exterior of the container 12. The arrangement 11 further includes an output duct 22 for the flowable substance which is to be discharged via the discharge valve 18, the output duct 22 originating at the container 12 and having a main shutoff valve 25 incorporated therein. Furthermore, the discharging arrangement 11 includes a central conduit 24 for conducting sterilizing steam or a similar sterilizing medium supplied from a source S. The central conduit 24 supplies the sterilizing medium to various components of the discharge arrangement 11, as will be discussed below. Additionally, the arrangement 11 includes a return conduit 26 for the discharge of the steam which has been used for the sterilizing operation, and of any condensate, from the discharging arrangement 11. The conduit 22 for the flowable substance, as well as the hot steam conduit 24 and the discharge valve 18, are so constructed that no undercut spaces or other eddy-current chambers or spaces are located in the path of the flowing sterilizing hot steam.

Figure 4:
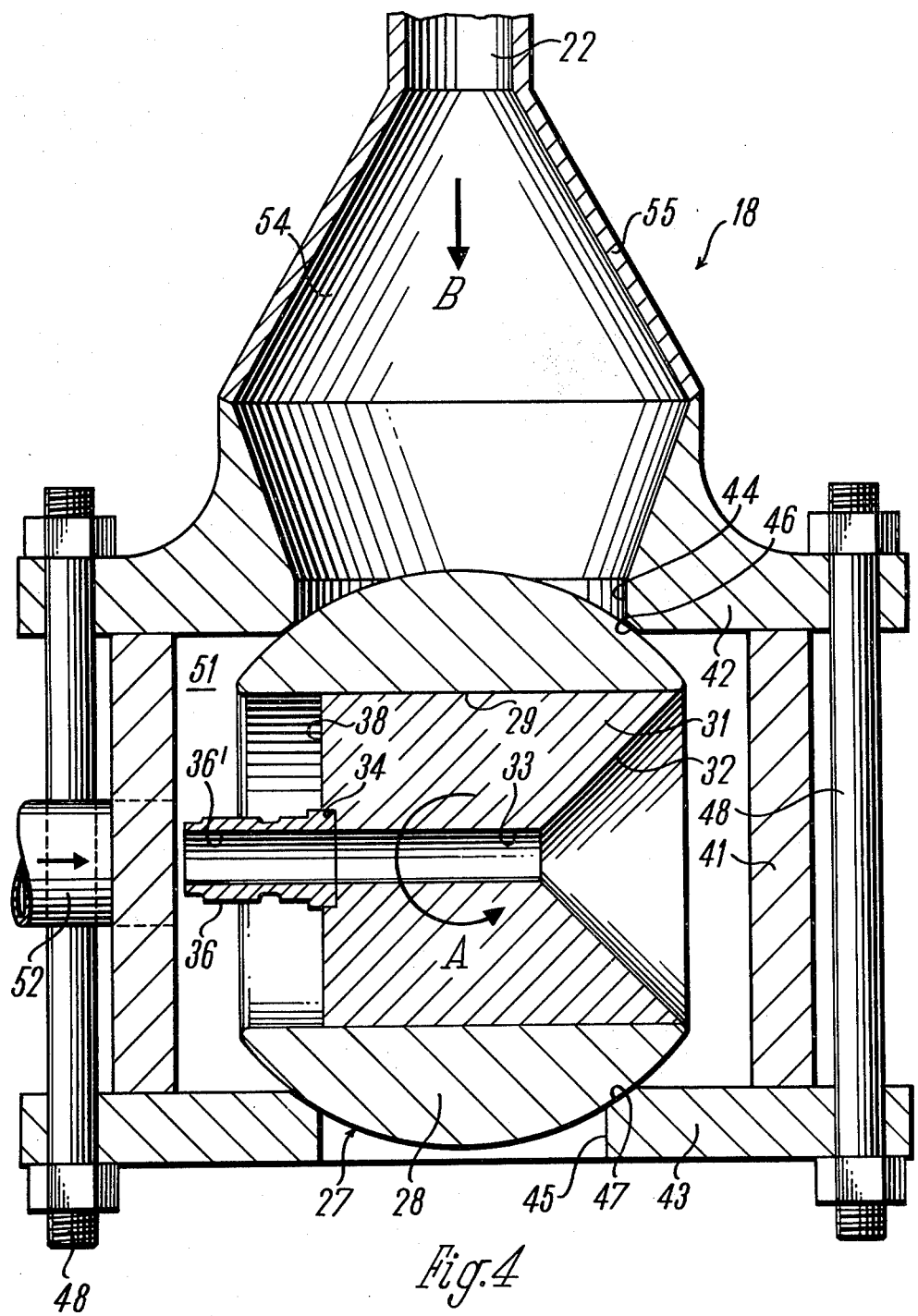
FIG. 4 is a sectional view taken on line IV—IV of FIG. 3.

As can be seen particularly in FIGS. 3 and 4, a correspondingly modified, but otherwise conventionally constructed and commercially available, ball valve 18 is used in the discharging arrangement 11. The discharge valve 18 includes a spherical valve member 27 which, in the illustrated embodiment, consists of several components in that it includes a ball 28 which is provided with a large-diameter through bore or passage 29, in which there is accommodated a cylindrical insert 31. The insert 31 is preferably welded to the ball 28 and has an axial length which is preferably less than that of the bore 29. The insert 31 is formed, at its inlet and, with an opening 32 which converges in the downstream direction, that is, leftwardly as seen in FIGS. 3 and 4. The largest diameter of this opening 32 substantially corresponds to the diameter of the bore or passage 29, while the frustoconical opening 32 merges into a bore 33 of a diameter considerably smaller than that of the passage 29 at its inner or leftward end. The bore 33 passes through the cylindrical insert 31 and is provided, at its other end, with a cylindrical enlargement 34. A nipple 36 is introduced into and preferably welded or soldered in the enlarged portion 34 of the bore 33. As may be seen in FIG. 2, the nipple 36 constitutes one part of a quick-release coupling 37 for the connection of the sterilized steam conduit 16 or a similar conduit. In the illustrated example of the embodiment of the present invention, the rapid-release coupling 37 is constructed as a plug-and-socket coupling and, consequently, the nipple 36 is constructed as a plug-type nipple. A surface 38 of the cylindrical insert 31 which is located opposite to the frustoconical opening 32 is so offset with respect to the outer surface of the ball 28 or the end of the passage 29, that the nipple 36, which is provided with a through bore 36' merging into the bore 33 of the insert 31, does not extend beyond the diameter of the ball 28; in other words, the outer end of the nipple 36 is located within the confines of an imaginary sphere along which the spherical surface of the ball 28 extends. However, it will be appreciated that the valve member 27, except for the nipple 26, could also be made of one piece. The valve member 27 is situated in a chamber bounded by a cylindrical housing 41 the inner radius of which substantially corresponds to the radius of the spherical valve member 27 and which is closed at its axial ends by respective flanges 42 and 43. The flanges 42 and 43 are respectively provided with ports 44 and 45 which are surrounded by annular seat surfaces 46 and 47 which sealingly contact the ball 28. It will be appreciated that a sealing ring could be situated between the respective seat surface 46 or 47 and the ball 28 if the sealing action of the contact of the seating surfaces 46 or 47 with the valve member 28 were insufficient. The flanges 42 and 43 are connected and drawn toward one another by bolts or similar connectors 48, so that the cylindrical valve housing 41 is sealingly clamped between the flanges 42 and 43. The components 41 to 43 together constitute a valve housing bounding a chamber, and the ball 28 can be rotated in the chamber through 90° as indicated by arrow A in FIG. 4 by means of a pin-shaped projection 49 (shown in FIG. 3) of the shaft 21, which is accommodated in a recess 50 of the ball 28 in such a manner as to transmit motion from the shaft 21 to the ball 28.

FIG. 4 illustrates that position of the discharge valve 18 in which the spherical valve member 27 sealingly closes both the inlet port 44 in the flange 42 and the outlet bore 45 in the flange 43. Thus, in this position, the coupling nipple 36 for the connection of the hose 16, which is integrated into the valve member 27, is located within a compartment 51 which is bounded by the valve member 27, on the one hand, and by the flanges 42, 43, and the cylindrical housing 41, on the other hand. As seen in particular in FIG. 3, a branch 52 of the central sterilizing steam conduit 24 opens into this space 51, preferably approximately along the longitudinal central plane and at an angle from above. As a comparison of FIGS. 2 and 4 will reveal, another branch 53 of the central sterilizing steam conduit 24 communicates, via an interposed valve 23, through the conduit 22, with a space 54 which is bounded by the flange 42 and a diverging conduit portion 55 connected to the flange 42 and communicating, at its small-diameter end, with the conduit 22 for the flowable substance to be discharged. As shown in FIG. 2, this branch 53 of the conduit 24 leads back from a location close to the discharge valve 18 and opens into the flowable substance conduit 22 downstream of the closing valve 23 and also downstream of the main shutoff valve 25. As a matter of fact, the branch 53 communicates with the conduit 22 in a region of curvature of the latter out of the vertical, from above, at an angle of about 10° with respect to the shutoff valve 25. As shown in FIGS. 2 and 3, an opening for the conduit 26 is provided both at the bottom of the valve space 51 and in the bottom of the space 54. The conduit 26 has two branches 26' and 26'' which respectively serve for conducting the spent steam and the condensate.

Having so described the construction of the arrangement 11 of the present invention as well as of the apparatus in which the arrangement 11 is employed, the sterilizing operation which is performed in accordance with the present invention will now be discussed.

It is assumed that a batch of a flowable substance which is to be discharged and dispensed into packaging units or receptacles has been produced and sterilized in the container 12. The main shutoff valve 25 in the conduit 22 for the flowable substance to be discharged is closed. A closing valve 56 is interposed in the conduit 24 for the supply of the hot sterilizing steam upstream from the beginning of the two branches 52 and 53. An adjustable throttling valve 57 is also interposed in the conduit 24 between the closing valve 56 and the two branches 52 and 53. At this time, that is, at the beginning of the sterilizing operation, the closing valve 56 is open and the throttling valve 57 lets the hot sterilizing steam pass therethrough without any appreciable throttling. As a result of this, the hot sterilizing steam is able to flow through the branch 53 and the open valve 23 into the output conduit or duct 22 and into the space 54 in order to sterilize this region, before it escapes from the interior of the discharge valve 18 through the conduit 26. Inasmuch as the sterilizing steam and its condensate are being steadily discharged through the conduit 26 after having acted on the respective exposed surfaces of the various components situated along the path of flow of the sterilizing steam, there is assured a steady flow of this sterilizing steam in its path. The hot sterilizing steam also flows through the branch 52 into the compartment 51, wherein it sterilizes not only the openings or passages 32, 33 and 36' of the valve member 28 and of the nipple 36, but also the outer surface of the nipple 36. Consequently, the entire discharge valve 18 is completely sterilized in this position of the valve member 27, inasmuch as the hot sterilizing steam flows past the outer surfaces of the valve member 28, as well as past the inner surfaces of the ball 28, the insert 38, the nipple 36, and the housing 41 to 43, as well as past the critical outer surface of the coupling nipple 36.

After a predetermined period of time which is necessary for the complete sterilization, the throttling valve 57 is adjusted so that it provides for a throttled supply of the hot sterilizing steam. The throttling valve 57 is preferably also constructed as a ball valve, the valve member of which is provided with a first bore of a large cross-sectional area, and with a second bore of a small cross-sectional area extending transversely to the first bore. Simultaneously with or subsequently to the adjustment of the position of the throttling valve 57 to its throttling position, also the discharge valve 18 is so adjusted as to its position that the ball 28 is rotated in the direction of the arrow A through 90°. As a result of this, the frustoconical opening 32 faces the inlet port 44 of the flange 42 and the coupling nipple 36 is in register with the outlet port 45 of the flange 43, thus being accessible from the exterior of the discharge valve 18, as indicated in FIG. 2. The throttled supply of the hot sterilizing steam renders it possible to maintain the above-mentioned regions or surfaces in sterilized condition during the rotation of the valve member 27 toward its open position, and, in particular, it prevents unsterile ambient atmosphere from flowing toward and reaching the compartment 51 and the nipple 36. The throttling is also necessary in order not to expose the person who is to attach the sterilized steam hose 16 to the coupling nipple 36 to the danger of injury. Thus, the throttled supply of the sterilizing steam is continued at least until the hose 16, which has been previously sterilized in a different device, is connected to the coupling nipple 36. Inasmuch as the hot sterilizing steam does not inflict any damage to the flowable substance to be filled, it is also possible to continue the admission of the sterilizing steam for a short interval following the opening of the main shutoff valve 25. During the discharging operation of the arrangement 11, the valve 23 in the branch 53 is closed under all circumstances, in order to assure that none of the product, that is, of the flowable substance being discharged, can flow into the same. Now, it is sufficient to close the closing valve 56 in the conduit 24 for the supply of the hot sterilizing steam and to open the valve 25 for the supply of the flowable substance to be discharged to cause the flowable substance to flow through the discharging arrangement 11 into the hose 16 the other end of which is arranged in a sterile space in which the packaging of the flowable substance into receptacles of predetermined sizes takes place. Once the respective batch contained in the container 12 is completely discharged, the apparatus 10 and the discharging arrangement 11 are again cleansed and sterilized with hot sterilizing steam, so that a new batch of the flowable substance can be produced. Thus, prior to the discharging of this new charge or batch of the flowable substance, the discharging arrangement 11 of the present invention is again sterilized in the above-discussed manner. A conduit 58 which is shown in FIG. 2 serves for the withdrawal of the condensate from the jacket of the container 12.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art, and therefore, such adaptations should and are intended to be comprehended within the meaning and range of equivalence of the claims.

I claim:

1. An arrangement for aseptically discharging a flowable substance, especially such which has been sterilized in a sterilizing container, into a sterilized conduit, comprising an output duct for the flowable substance having an output end; a discharge valve arranged at and communicating with said output end of said duct and including a valve housing bounding a chamber and inlet and outlet ports for the flowable substance, and having valve seats surrounding said ports, and a valve member received in said chamber and having a surface located on an imaginary sphere and sealingly contacting said seats, and a through passage having inlet and outlet ends, said valve member being rotatable between an open position in which said ends of said passage respectively register with said ports, and a closed position; means for coupling said discharge valve to the sterilized conduit, including a tubular coupling member mounted on said valve member in communication with said outlet end of said passage and having a portion extending beyond the latter and terminating within the confines of said imaginary sphere; and means for admitting sterilizing medium between said valve housing and said valve member at the region of said coupling member.

2. The arrangement as defined in claim 1, wherein said sterilizing medium is steam.

3. The arrangement as defined in claim 1, further comprising means for mounting said coupling member on said valve member, including an insert accommodated in said passage of said valve member and supporting said coupling member.

4. The arrangement as defined in claim 3, wherein said insert is rigidly connected to said valve member and to said coupling member.

5. The arrangement as defined in claim 3, wherein said insert includes an opening which communicates with said inlet port in said open position of said valve member and with said coupling member.

6. The arrangement as defined in claim 5, wherein said opening of said insert converges from said inlet end of said passage toward said coupling member.

7. The arrangement as defined in claim 1, wherein said valve member is rotatable about a substantially vertical axis; and wherein said admitting means includes an admitting duct which extends into said chamber at an acute angle from above to the horizontal.

8. The arrangement as defined in claim 7, wherein said acute angle amounts to substantially 30°.

9. The arrangement as defined in claim 1, wherein said valve member in said closed position delimits in said chamber of said valve housing a compartment surrounding said coupling member; and wherein said sterilizing means includes an admitting duct communicating with said compartment.

10. The arrangement as defined in claim 9; and further comprising means for conducting spent sterilizing medium out of said compartment.

11. The arrangement as defined in claim 10, wherein said compartment extends to the lowest part of said valve housing; and wherein said means for conducting the spent sterilizing medium passes through said lower part of said valve housing.

12. The arrangement as defined in claim 1; and further comprising means for sterilizing said discharge valve at said inlet port, including a sterilizing conduit communicating with said output duct and admitting sterilizing medium thereinto.

13. The arrangement as defined in claim 12, wherein said sterilizing conduit and said output duct converge toward their junction as considered in the directions of flow therethrough.

14. The arrangement as defined in claim 13, wherein the angle of convergence amounts to substantially 10°.

15. The arrangement as defined in claim 12 for use in a sterilizing installation in which a main shutoff valve for the flowable substance is arranged at the other end of said output duct, wherein said sterilizing conduit opens into said other end of said duct immediately downstream of said main valve.

16. The arrangement as defined in claim 12, wherein said admitting means and said sterilizing means each includes a sterilizing medium conduit and an adjustable throttling valve in the respective sterilizing medium conduit.

17. The arrangement as defined in claim 1, wherein said coupling is a rapid-release coupling.

18. The arrangement as defined in claim 17, wherein said rapid-release coupling is a plug-and-socket coupling.

* * * * *